(12) United States Patent
Song et al.

(10) Patent No.: US 12,325,748 B2
(45) Date of Patent: Jun. 10, 2025

(54) BIFUNCTIONAL FUSION PROTEIN AGAINST PDL1 AND TGFβ AND USE THEREOF

(71) Applicant: Shandong Boan Biotechnology Co., Ltd., Yantai (CN)

(72) Inventors: Deyong Song, Yantai (CN); Hongguang Xu, Yantai (CN); Zhen Han, Yantai (CN)

(73) Assignee: Shandong Boan Biotechnology Co., Ltd., Yantai (CN)

( * ) Notice: Subject to any disclaimer, the term of this patent is extended or adjusted under 35 U.S.C. 154(b) by 815 days.

(21) Appl. No.: 17/601,891

(22) PCT Filed: Jun. 8, 2020

(86) PCT No.: PCT/CN2020/094855
§ 371 (c)(1),
(2) Date: Oct. 6, 2021

(87) PCT Pub. No.: WO2020/248926
PCT Pub. Date: Dec. 17, 2020

(65) Prior Publication Data
US 2022/0213195 A1    Jul. 7, 2022

(30) Foreign Application Priority Data
Jun. 10, 2019  (CN) .......... 201910497064.X
Jun. 10, 2019  (CN) .......... 201910497723.X

(51) Int. Cl.
| | | |
|---|---|---|
| C07K 16/28 | (2006.01) |
| A61P 35/00 | (2006.01) |
| C07K 14/71 | (2006.01) |
| C12N 15/85 | (2006.01) |
| A61K 39/00 | (2006.01) |

(52) U.S. Cl.
CPC .......... *C07K 16/2827* (2013.01); *A61P 35/00* (2018.01); *C07K 14/71* (2013.01); *C12N 15/85* (2013.01); *A61K 2039/505* (2013.01); *C07K 2317/31* (2013.01); *C07K 2317/622* (2013.01); *C07K 2317/76* (2013.01); *C07K 2317/92* (2013.01); *C07K 2319/32* (2013.01)

(58) Field of Classification Search
CPC .............. C07K 16/2827; C07K 14/71; C07K 2317/31; C07K 2317/622; C07K 2317/76; C07K 2317/92; C07K 2319/32; C07K 16/22; C07K 16/468; A61P 35/00; C12N 15/85; A61K 2039/505; A01K 2207/15; A01K 2227/105; A01K 2267/0331; G01N 33/574
See application file for complete search history.

(56) References Cited

U.S. PATENT DOCUMENTS

| | | |
|---|---|---|
| 2013/0323249 A1 | 12/2013 | Zhou et al. |
| 2015/0225483 A1 | 8/2015 | Lo |
| 2017/0058033 A1 | 3/2017 | Ludwig et al. |

FOREIGN PATENT DOCUMENTS

| | | |
|---|---|---|
| CN | 103571872 B | 11/2016 |
| CN | 106103488 | 11/2016 |
| CN | 109641963 | 4/2019 |
| JP | 2008-544755 | 12/2008 |
| JP | 2015-500207 | 1/2015 |
| JP | 2015-519375 A | 7/2015 |
| JP | 2017-506217 | 5/2017 |
| JP | 2017-536099 A | 12/2017 |
| JP | 2018-527949 | 9/2018 |
| JP | 2018-531219 A | 10/2018 |
| JP | 2019-503687 A | 2/2019 |
| JP | 2013-511959 | 4/2023 |
| WO | WO 2007005874 | 1/2007 |
| WO | WO 2011066389 | 6/2011 |
| WO | WO 2013079174 | 6/2013 |
| WO | WO 2016061142 | 4/2016 |
| WO | WO 2017020291 | 2/2017 |
| WO | WO 2018129331 | 7/2018 |
| WO | WO 2018205985 | 11/2018 |
| WO | WO 2018218215 | 11/2018 |
| WO | WO 2019101196 | 5/2019 |

OTHER PUBLICATIONS

Bierie et al., "TGFβ: the molecular Jekyll and Hyde of cancer," Nat Rev Cancer, Jul. 2006, 6(7):506-20.
ClinicalTrials.gov [online], "MSB0011359C (M7824) in Metastatic or Locally Advanced Solid Tumors" NCT02517398, last updated Jun. 15, 2022, retrieved on Jul. 5, 2022, retrieved from URLhttps://clinicaltrials.gov/ct2/show/NCT02517398, 14 pages.
Extended European Search Report in European Appln. No. 20822451.9, dated May 25, 2022, 16 pages.
International Preliminary Report on Patentability in International Appln. No. PCT/CN2020/094855, dated Dec. 14, 2021, 12 pages.
International Search Report and Written Opinion in International Appln. No. PCT/CN2020/094855, dated Sep. 10, 2020, 20 pages.
Iwai et al., "Involvement of PD-L1 on tumor cells in the escape from host immune system and tumor immunotherapy by PD-L1 blockade," PNAS, Sep. 2002, 99(19):12293-7.

(Continued)

*Primary Examiner* — Misook Yu
*Assistant Examiner* — Grace H Lunde
(74) *Attorney, Agent, or Firm* — Fish & Richardson P.C.

(57) ABSTRACT

Provided are an anti-PDL1 antibody and an antigen-binding fragment thereof, and further provided are a bifunctional fusion protein against PDL1 and TGFβ and a preparation method thereof and the use thereof. The antibody or antigen-binding fragment or the bifunctional fusion protein has one or more of the following advantages: an enhanced TGFβ1 binding activity, an enhanced affinity to PDL1, an enhanced ability to block the binding of PDL1 and PD1, an enhanced functional activity for blocking TGFβ 1, an enhanced ability to promote the secretion of IFN-γ by T cells, a better immunomodulatory effect and a better tumor inhibitory effect.

6 Claims, 3 Drawing Sheets

Specification includes a Sequence Listing.

(56) References Cited

OTHER PUBLICATIONS

Lin et al., "The Soluble Exoplasmic Domain of the Type II Transforming Growth Factor (TGF)-β Receptor: A Heterogeneously Glycosylated Protein With High Affinity and Selectivity for TGF-β Ligands," J Biol Chem, Feb. 1995, 270(6):2747-54.
Ohigashi et al., "Clinical significance of programmed death-1 ligand-1 and programmed death-1 ligand-2 expression in human esophageal cancer," Clin Cancer Res, Apr. 2005, 11(8):2947-53.
Ravi et al., "Bifunctional immune checkpoint-targeted antibody-ligand traps that simultaneously disable TGFβ enhance the efficacy of cancer immunotherapy," Nature Communications, Feb. 2018, 9:741, 14 pages.
Suzuki et al., "Soluble type II transforming growth factor-β receptor inhibits established murine malignant mesothelioma tumor growth by augmenting host antitumor immunity," Clin Cancer Res, Sep. 2004, 10(17):5907-18.

SEQUENCE LISTING

<160> NUMBER OF SEQ ID NOS: 35

<210> SEQ ID NO 1
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 1

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
                100                 105                 110

Lys

<210> SEQ ID NO 2
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 2

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Ile Ile Thr Tyr Ala Gly Ser Asn Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Arg Asp Arg Ile Trp Val Asp Tyr Trp Gly Gln Gly Thr Leu Val
                100                 105                 110

Thr Val Ser Ser
            115

<210> SEQ ID NO 3
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 3

```
Asp Ile Val Met Thr Gln Ser Pro Asp Ser Leu Ala Met Ser Leu Gly
1               5                   10                  15

Glu Arg Ala Thr Ile Asn Cys Lys Ser Ser Gln Ser Val Leu Tyr Asn
            20                  25                  30

Ser Asn Asn Lys Asn Tyr Leu Ala Trp Tyr Gln Gln Lys Pro Gly Gln
        35                  40                  45

Pro Pro Lys Leu Leu Thr Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Leu Pro Leu Thr Phe Gly Gly Gly Thr Lys Val Glu Ile
            100                 105                 110

Lys
```

<210> SEQ ID NO 4
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 4

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Tyr Phe Asp Tyr Trp Gly Gln Gly Thr Leu Val
            100                 105                 110

Thr Val Ser Ser
        115
```

<210> SEQ ID NO 5
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 5

```
Gln Ser Val Leu Tyr Ser Ser Asn Asn Lys Asn Tyr
1               5                   10
```

<210> SEQ ID NO 6
<211> LENGTH: 3
<212> TYPE: PRT
<213> ORGANISM: Artificial Sequence
<220> FEATURE:
<223> OTHER INFORMATION: The sequence is artificially synthesized

<400> SEQUENCE: 6

Trp Ala Ser
1

<210> SEQ ID NO 7
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 7

Gln Gln Tyr Tyr Ser Thr Pro Leu Thr
1               5

<210> SEQ ID NO 8
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 8

Gly Phe Thr Phe Ser Asn Tyr Ala
1               5

<210> SEQ ID NO 9
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 9

Ile Thr Tyr Ala Gly Ser Asn Glu
1               5

<210> SEQ ID NO 10
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 10

Ala Arg Asp Arg Ile Trp Val Asp Tyr
1               5

<210> SEQ ID NO 11
<211> LENGTH: 12
<212> TYPE: PRT
<213> ORGANISM: Artificial Sequence
<220> FEATURE:
<223> OTHER INFORMATION: The sequence is artificially synthesized

<400> SEQUENCE: 11

Gln Ser Val Leu Tyr Asn Ser Asn Asn Lys Asn Tyr
1               5                   10

<210> SEQ ID NO 12
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 12

Gln Gln Tyr Tyr Ser Leu Pro Leu Thr
1               5

<210> SEQ ID NO 13
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 13

Gly Phe Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: The sequence is artificially synthesized

<400> SEQUENCE: 14

Ile Ser Tyr Asp Gly Ser Asn Lys
1               5

<210> SEQ ID NO 15
<211> LENGTH: 9
<212> TYPE: PRT
<213> ORGANISM: Artificial Sequence
<220> FEATURE:
<223> OTHER INFORMATION: The sequence is artificially synthesized

<400> SEQUENCE: 15

Ala Arg Asp Arg Ile Tyr Phe Asp Tyr
1               5

<210> SEQ ID NO 16
<211> LENGTH: 107
<212> TYPE: PRT
<213> ORGANISM: Artificial Sequence
<220> FEATURE:
<223> OTHER INFORMATION: The sequence is artificially synthesized

<400> SEQUENCE: 16

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 17
<211> LENGTH: 330
<212> TYPE: PRT
<213> ORGANISM: Artificial Sequence
<220> FEATURE:

<223> OTHER INFORMATION: The sequence is artificially synthesized

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 487
<212> TYPE: PRT
<213> ORGANISM: Artificial Sequence
<220> FEATURE:
<223> OTHER INFORMATION: The sequence is artificially synthesized

<400> SEQUENCE: 18

Ala Ser Thr Lys Gly Pro Ser Val Phe Pro Leu Ala Pro Ser Ser Lys
1               5                   10                  15

-continued

```
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Gln Thr
 65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Ala Gly Gly Gly Gly Ser Gly
                325                 330                 335
Gly Gly Gly Ser Gly Gly Gly Gly Ser Gly Gly Gly Gly Ser Gly Ile
            340                 345                 350
Pro Pro His Val Gln Lys Ser Val Asn Asn Asp Met Ile Val Thr Asp
            355                 360                 365
Asn Asn Gly Ala Val Lys Phe Pro Gln Leu Cys Lys Phe Cys Asp Val
            370                 375                 380
Arg Phe Ser Thr Cys Asp Asn Gln Lys Ser Cys Met Ser Asn Cys Ser
385                 390                 395                 400
Ile Thr Ser Ile Cys Glu Lys Pro Gln Glu Val Cys Val Ala Val Trp
                405                 410                 415
Arg Lys Asn Asp Glu Asn Ile Thr Leu Glu Thr Val Cys His Asp Pro
            420                 425                 430
```

```
Lys Leu Pro Tyr His Asp Phe Ile Leu Glu Asp Ala Ala Ser Pro Lys
            435                 440                 445

Cys Ile Met Lys Glu Lys Lys Pro Gly Thr Phe Phe Met Cys
450                 455                 460

Ser Cys Ser Ser Asp Glu Cys Asn Asp Asn Ile Ile Phe Ser Glu Glu
465                 470                 475                 480

Tyr Asn Thr Ser Asn Pro Asp
                485
```

<210> SEQ ID NO 19
<211> LENGTH: 120
<212> TYPE: PRT
<213> ORGANISM: Artificial Sequence
<220> FEATURE:
<223> OTHER INFORMATION: The sequence is artificially synthesized

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Met Trp Val Arg Gln Ala Pro Gly Lys Gly Leu Glu Trp Val
        35                  40                  45

Ser Ser Ile Tyr Pro Ser Gly Gly Ile Thr Phe Tyr Ala Asp Thr Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ile Lys Leu Gly Thr Val Thr Val Asp Tyr Trp Gly Gln
            100                 105                 110

Gly Thr Leu Val Thr Val Ser Ser
        115                 120
```

<210> SEQ ID NO 20
<211> LENGTH: 110
<212> TYPE: PRT
<213> ORGANISM: Artificial Sequence
<220> FEATURE:
<223> OTHER INFORMATION: The sequence is artificially synthesized

<400> SEQUENCE: 20

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Arg Val Phe Gly Thr Gly Thr Lys Val Thr Val Leu
            100                 105                 110
```

<210> SEQ ID NO 21

```
<211> LENGTH: 106
<212> TYPE: PRT
<213> ORGANISM: Artificial Sequence
<220> FEATURE:
<223> OTHER INFORMATION: The sequence is artificially synthesized

<400> SEQUENCE: 21

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 22
<211> LENGTH: 330
<212> TYPE: PRT
<213> ORGANISM: Artificial Sequence
<220> FEATURE:
<223> OTHER INFORMATION: The sequence is artificially synthesized

<400> SEQUENCE: 22

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
```

```
                210                 215                 220
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Ala
                325                 330

<210> SEQ ID NO 23
<211> LENGTH: 136
<212> TYPE: PRT
<213> ORGANISM: Artificial Sequence
<220> FEATURE:
<223> OTHER INFORMATION: The sequence is artificially synthesized

<400> SEQUENCE: 23

Ile Pro Pro His Val Gln Lys Ser Val Asn Asn Asp Met Ile Val Thr
1               5                   10                  15

Asp Asn Asn Gly Ala Val Lys Phe Pro Gln Leu Cys Lys Phe Cys Asp
            20                  25                  30

Val Arg Phe Ser Thr Cys Asp Asn Gln Lys Ser Cys Met Ser Asn Cys
        35                  40                  45

Ser Ile Thr Ser Ile Cys Glu Lys Pro Gln Glu Val Cys Val Ala Val
    50                  55                  60

Trp Arg Lys Asn Asp Glu Asn Ile Thr Leu Glu Thr Val Cys His Asp
65                  70                  75                  80

Pro Lys Leu Pro Tyr His Asp Phe Ile Leu Glu Asp Ala Ala Ser Pro
                85                  90                  95

Lys Cys Ile Met Lys Glu Lys Lys Pro Gly Glu Thr Phe Phe Met
            100                 105                 110

Cys Ser Cys Ser Ser Asp Glu Cys Asn Asp Asn Ile Ile Phe Ser Glu
            115                 120                 125

Glu Tyr Asn Thr Ser Asn Pro Asp
            130                 135

<210> SEQ ID NO 24
<211> LENGTH: 21
<212> TYPE: PRT
<213> ORGANISM: Artificial Sequence
<220> FEATURE:
<223> OTHER INFORMATION: The sequence is artificially synthesized

<400> SEQUENCE: 24

Gly Gly Gly Gly Ser Gly Gly Gly Gly Ser Gly Gly Gly Gly Ser Gly
1               5                   10                  15

Gly Gly Ser Gly
            20

<210> SEQ ID NO 25
<211> LENGTH: 113
```

```
<212> TYPE: PRT
<213> ORGANISM: Artificial Sequence
<220> FEATURE:
<223> OTHER INFORMATION: The sequence is artificially synthesized

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Ile Thr Phe Gly Gln Gly Thr Lys Leu Glu Ile
            100                 105                 110

Lys

<210> SEQ ID NO 26
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 26

Glu Leu Val Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Asp Ile
            100                 105                 110

Lys

<210> SEQ ID NO 27
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 27

Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30
```

```
Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Ile Arg Asp Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Ala Ala Val Tyr Tyr Cys Gln Gln
                 85                  90                  95

Phe Tyr Ser Ile Pro Leu Thr Phe Gly Gly Gly Thr Lys Val Glu Ile
                100                 105                 110

Lys
```

```
<210> SEQ ID NO 28
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 28

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Asp Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Ile Pro Leu Thr Phe Gly Gly Gly Thr Lys Val Glu Ile
                100                 105                 110

Lys
```

```
<210> SEQ ID NO 29
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 29

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Ile Pro Leu Thr Phe Gly Gly Gly Thr Lys Val Glu Ile
```

100                 105                 110
Lys

<210> SEQ ID NO 30
<211> LENGTH: 113
<212> TYPE: PRT
<213> ORGANISM: Artificial Sequence
<220> FEATURE:
<223> OTHER INFORMATION: The sequence is artificially synthesized

<400> SEQUENCE: 30

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Asp Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Phe Pro Leu Thr Phe Gly Gly Gly Thr Lys Val Glu Ile
            100                 105                 110
Lys

<210> SEQ ID NO 31
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 31

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Tyr Phe Asp Tyr Trp Gly Gln Gly Thr Leu Val
            100                 105                 110

Thr Val Ser Ser
        115

<210> SEQ ID NO 32
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 32

Glu Val Gln Leu Val Gln Ser Gly Gly Gly Val Val Gln Pro Gly Lys
1               5                   10                  15

Ser Leu Arg Leu Ser Cys Ala Ala Ser Gly Phe Thr Phe Ser Ser Tyr
            20                  25                  30

Ser Met His Trp Val Arg Gln Ala Pro Gly Lys Gly Leu Glu Trp Val
        35                  40                  45

Ala Leu Ile Ser Phe Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Thr Glu Asp Thr Ala Val Tyr Tyr Cys
                85                  90                  95

Ala Arg Asp Arg Ile Tyr Leu Asp Tyr Trp Gly Gln Gly Thr Leu Val
            100                 105                 110

Thr Val Ser Ser
        115

<210> SEQ ID NO 33
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 33

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Ala Met His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Tyr Phe Asp Tyr Trp Gly Gln Gly Thr Leu Val
            100                 105                 110

Thr Val Ser Ser
        115

<210> SEQ ID NO 34
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 34

Glu Val Gln Leu Val Gln Ser Gly Gly Gly Val Val Gln Pro Gly Arg
1               5                   10                  15

Ser Leu Arg Leu Ser Cys Ala Ala Ser Gly Ile Thr Phe Ser Asn Tyr
            20                  25                  30

Ala Met His Trp Val Arg Gln Ala Pro Gly Lys Gly Leu Glu Trp Val
        35                  40                  45

```
Ala Leu Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Tyr Phe Asp Tyr Trp Gly Gln Gly Thr Leu Val
                100                 105                 110

Thr Val Ser Ser
        115

<210> SEQ ID NO 35
<211> LENGTH: 116
<212> TYPE: PRT
<213> ORGANISM: Artificial Sequence
<220> FEATURE:
<223> OTHER INFORMATION: The sequence is artificially synthesized

<400> SEQUENCE: 35

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Ala Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ile Phe Phe Asp Tyr Trp Gly Gln Gly Thr Leu Val
                100                 105                 110

Thr Val Ser Ser
        115
```

BIFUNCTIONAL FUSION PROTEIN AGAINST PDL1 AND TGFβ AND USE THEREOF

CROSS-REFERENCE TO RELATED APPLICATIONS

This application is a National Stage application under 35 U.S.C. § 371 of International Application No. PCT/CN2020/094855, filed on Jun. 8, 2020, which claims priority to Chinese Application No. 201910497064.X, filed on Jun. 10, 2019, and Chinese Application No. 201910497723.X, filed on Jun. 10, 2019, the contents of which are incorporated herein by reference in their entirety.

SEQUENCE LISTING

The instant application contains a Sequence Listing which has been submitted electronically in ASCII format and is hereby incorporated by reference in its entirety. Sais ASCII copy, created on Mar. 13, 2025, is named 48644-0005US1_ST25 and is 35,631 bytes in size.

TECHNICAL FIELD

The invention relates to the technical field of biomedicine or biopharmaceuticals. Specifically, the present invention relates to anti-PDL1 antibodies, bifunctional fusion proteins against PDL1 and TGFβ, and variants and antigen-binding fragments thereof, as well as a preparation method thereof and methods and uses for treating cancer.

BACKGROUND

PD1 (programmed cell death-1) and PDL1 (programmed cell death-1 ligand 1) are an important kind of immune checkpoint proteins, wherein PD1 is expressed on the surface of activated T cells and NK cells, and tumor cell inhibits maturation and proliferation of T cell and NK cell after bonding to PD1 by expressing PDL1 in large quantities, and then escapes from immune surveillance (Iwai et al., PNAS 99:12293-7, 2002) (Ohigashi et al., Clin Cancer Res 11:2947-53, 2005). Therefore, by blocking the interaction between PD1 and PDL1, T cells can be reactivated, and the tumor cells can be identified and killed to benefit the patient.

TGFβ can inhibit the growth of early tumors, but as the tumor continues to progress, the tumor cells become no longer sensitive to TGFβ, and at this time, TGFβ in turn promotes tumor growth by promoting epithelial-stromal transfer and suppressing the immune system (Bierie et al., Nat Rev Cancer. 2006; 6:506-20).

The extracellular domain of TGFβRII is only 136 amino acid residues in length and the TGFβRII can bind TGFβ1 (Lin et al., J Biol Chem. 1995; 270:2747-54). Soluble TGFβRII-Fc has been tested as an anticancer agent and has been shown that it can inhibit the growth of malignant mesothelioma in a murine model (Suzuki et al., Clin Cancer Res. 2004; 10:5907-18) (Suzuki et al., Clin Cancer Res. 2004; 10:5907-18).

M7824 bifunctional fusion protein from the company Merck (Chinese application number CN201580007865.3) is anti-PDL1 antibody Avelumab linked to TGFβRII by $(G_4S)_4G$ (SEQ ID NO: 24), some phase I and phase II clinical trials have been completed, and it has performed well in a variety of solid tumors (MSB0011359C).

However, in the face of the patient's medicinal demands for disease treatment, especially demands for antibody drugs, there is still an urgent clinical need to provide an anti-PDL1 antibody or bifunctional fusion protein against PDL1 and TGFβ with higher binding activity and better efficacy.

SUMMARY

In the full text of the present invention, various implementations regarding VL (light chain variable region), VH (heavy chain variable region), LCDR (light chain complementarity determining region), HCDR (heavy chain complementarity determining region), LCDR1, LCDR2, LCDR3, HCDR1, HCDR2 and HCDR3 can be implemented individually or in any combination.

The present invention relates to an antibody or antigen-binding fragment thereof, or bifunctional fusion protein and the preparation method and use thereof.

In an aspect of the present invention, the present invention relates to an antibody or antigen-binding fragment thereof including three heavy chain complementarity determining regions, wherein HCDR1 amino acid sequence is represented by SEQ ID NO: 8, HCDR2 amino acid sequence is represented by SEQ ID NO: 9, and the HCDR3 amino acid sequence is represented by SEQ ID NO: 10. Further, the antibody or antigen-binding fragment thereof also includes three light chain complementarity determining regions, wherein the LCDR1 amino acid sequence is represented by SEQ ID NO: 5, the LCDR2 amino acid sequence is represented by SEQ ID NO: 6, and the LCDR3 amino acid sequence is represented by SEQ ID NO: 7.

In an aspect of the present invention, the antibody or antigen-binding fragment thereof provided in the present invention includes a heavy chain variable region represented by SEQ ID NO: 2; preferably, further includes a light chain variable region represented by SEQ ID NO: 1.

In an aspect of the present invention, the present invention relates to an antibody or antigen-binding fragment thereof including three light chain complementarity determining regions, wherein the LCDR1 amino acid sequence is represented by SEQ ID NO: 11, the LCDR2 amino acid sequence is represented by SEQ ID NO: 6, and the LCDR3 amino acid sequence is represented by SEQ ID NO: 12; and/or three heavy chain complementarity determining regions, wherein the HCDR1 amino acid sequence is represented by SEQ ID NO: 13, the HCDR2 amino acid sequence is represented by SEQ ID NO: 14, and the HCDR3 amino acid sequence is represented by SEQ ID NO: 15.

In another aspect, the present invention relates to an antibody or antigen-binding fragment thereof including the light chain variable region of the amino acid sequence represented by SEQ ID NO: 3, and/or the heavy chain variable region of the amino acid sequence represented by SEQ ID NO: 4.

In another aspect, the sequence of the light chain constant region of the antibody or antigen-binding fragment thereof of any one of the preceding aspects is SEQ ID NO: 16.

In another aspect, the sequence of the heavy chain constant region of the antibody or antigen-binding fragment thereof of any one of the preceding aspects is SEQ ID NO: 17.

Specifically, the antibody or antigen-binding fragment thereof provided in the present invention preferably includes the light chain variable region of the amino acid sequence represented by SEQ ID NO: 1, the heavy chain variable region of the amino acid sequence represented by SEQ ID NO: 2, the light chain constant region of the amino acid sequence represented by SEQ ID NO: 16 and the heavy chain constant region of the amino acid sequence represented by SEQ ID NO: 17. Alternatively, the antibody or antigen-binding fragment thereof provided in the present invention preferably includes the light chain variable region of the amino acid sequence represented by SEQ ID NO: 3, the heavy chain variable region of the amino acid sequence represented by SEQ ID NO: 4, the light chain constant region of the amino acid sequence represented by SEQ ID NO: 16 and the heavy chain constant region of the amino acid sequence represented by SEQ ID NO: 17.

In another aspect, the present invention relates to the antibody or antigen-binding fragment thereof of any one of the preceding aspects including a monoclonal antibody, a polyclonal antibody, a chimeric antibody, a humanized antibody, a Fab fragment, a Fab' fragment, a F(ab')2 fragment, a Fv fragment, a scFv fragment, a dsFv fragment or the like.

In another aspect, any one of the above antibodies or antigen-binding fragments thereof binds PDL1.

In another aspect, the present invention relates to a bifunctional fusion protein including the antibody or antigen-binding fragment thereof of any one of the preceding aspects and a TGFβRII fragment, and preferably the TGFβRII fragment includes a TGFβRII extracellular domain.

In another aspect, in the bifunctional fusion protein, the antibody or antigen-binding fragment thereof of any one of the preceding aspects is linked to the TGFβRII fragment by a linker, preferably, the TGFβRII fragment is linked to a C-terminus of the heavy chain constant region of the antibody or antigen-binding fragment thereof, preferably by a $(G_4S)_4G$ (SEQ ID NO: 24) (i.e., GGGGSGGGGSGGGGSGGGGSG) (SEQ ID NO: 24) linker, preferably, the sequence of the heavy chain constant region of the bifunctional fusion protein is SEQ ID NO: 22, and preferably the sequence of the TGFβRII fragment of the bifunctional fusion protein is SEQ ID NO: 23; and specifically, the structure of the bifunctional fusion protein is: an antibody or antigen-binding fragment thereof-$(G_4S)_4G$ (SEQ ID NO: 24)-TGFβRII fragment.

In another aspect, in the bifunctional fusion protein, the sequence of the light chain variable region of the antibody or antigen-binding fragment thereof is SEQ ID NO: 1, the sequence of the heavy chain variable region is SEQ ID NO: 2, preferably, in the bifunctional fusion protein, the sequence of the light chain constant region is SEQ ID NO: 16, the sequence of the heavy chain constant region is SEQ ID NO: 22, and the sequence of the TGFβRII fragment is SEQ ID NO: 23; and specifically, the sequences of the heavy chain constant region and the TGFβRII fragment which are linked by $(G_4S)_4G$ (SEQ ID NO: 24) are SEQ ID NO: 18.

In another aspect, in the bifunctional fusion protein, the sequence of the light chain variable region of the antibody or antigen-binding fragment thereof is SEQ ID NO: 3, the sequence of the heavy chain variable region is SEQ ID NO: 4, preferably, in the bifunctional fusion protein, the sequence of the light chain constant region is SEQ ID NO: 16, the sequence of the heavy chain constant region is SEQ ID NO: 22, and the sequence of the TGFβRII fragment is SEQ ID NO: 23; and specifically, the sequences of the heavy chain constant region and the TGFβRII fragment which are linked by $(G_4S)_4G$ (SEQ ID NO: 24) are SEQ ID NO: 18.

In another aspect, any one of the above bifunctional fusion proteins binds PDL1 and TGFβ.

In another aspect, the present invention relates to a nucleic acid encoding the antibody or antigen-binding fragment thereof or the bifunctional fusion protein of any one of the preceding aspects.

In another aspect, the present invention relates to a vector including the nucleic acid of the preceding aspect, or the vector can express the antibody or antigen-binding fragment thereof or the bifunctional fusion protein of any one of the preceding aspects. Preferably, the vector may be a viral vector; preferably the viral vector includes but is not limited to a lentiviral vector, an adenovirus vector, an adeno-associated viral vector, a retroviral vector, or the like; preferably the vector may be a non-viral vector; preferably the vector may be a mammalian cell expression vector; preferably the expression vector may be a bacterial expression vector; and preferably the expression vector may be a fungal expression vector.

In another aspect, the present invention relates to a cell that can express a cell of the antibody or antigen-binding fragment thereof or the bifunctional fusion protein of any one of the preceding aspects. Preferably, the cell is a bacterial cell; preferably the bacterial cell is an *E. coli* cell and the like; preferably the cell is a fungal cell; preferably the fungal cell is a yeast cell; preferably the yeast cell is a *Pichia pastoris* and the like; preferably the cell is a mammalian cell; preferably the mammalian cell is a Chinese hamster ovary cell (CHO), a human embryonic kidney cell (293), a B cell, a T cell, a DC cell, a NK cell, or the like.

In another aspect, the present invention relates to a pharmaceutical composition including the antibody or antigen-binding fragment thereof, the bifunctional fusion protein, the nucleic acid, the vector or the cell of any one of the preceding aspects, preferably, the pharmaceutical composition further includes a pharmaceutically acceptable excipient, and preferably, the pharmaceutically acceptable excipient includes one or more of the following: a solvent, a dispersant, an additive, a plasticizer and the like which are pharmaceutically acceptable.

In another aspect, the pharmaceutical composition may further include other therapeutic agents. In some implementations, the other therapeutic agents include chemotherapeutic agents, immunotherapeutic agents, or hormonal therapeutic agents. The combined administration of the antibody or antigen-binding fragment and the other therapeutic agents can enhance the therapeutic effect.

In another aspect, the "enhance the therapeutic effect" refers to enhancing the therapeutic effect of other therapeutic agents or therapies. The antibody or antigen-binding fragment provided in the present invention can be administered individually or in combination with other therapeutic agents or therapies. In some implementations, the other therapeutic agents or therapies include chemotherapeutic agents, immunotherapeutic agents, hormonal therapeutic agents, radiation therapy and surgery.

In another aspect, there is provided a kit including the antibody or antigen-binding fragment thereof of the present invention, or including the bifunctional fusion protein, or including the nucleic acid encoding the antibody or antigen-binding fragment thereof or the bifunctional fusion protein.

In another aspect, the present invention relates to an application of the antibody or antigen-binding fragment thereof, the bifunctional fusion protein, the nucleic acid, the vector or the cell of any one of the preceding aspects in preparation of medicaments for treatment or prophylaxis of diseases.

In another aspect, the present invention relates to an application of the antibody or antigen-binding fragment thereof, the bifunctional fusion protein or the nucleic acid of any one of the preceding aspects in preparation of a diagnostic or detection kit.

In another aspect, there is provided a method of treating or preventing a disease including administering the antibody or antigen-binding fragment thereof, the bifunctional fusion protein, the nucleic acid, the vector, the cell or the pharmaceutical composition of any one of the preceding aspects to a subject in need.

In another aspect, there is provided a method of diagnosis or detection including administering the antibody or antigen-binding fragment thereof, the bifunctional fusion protein, the nucleic acid or the kit of any one of the preceding aspects to a subject in need or sample. Preferably, the method is a method of diagnosing or detecting diseases.

In another aspect, the present invention relates to the use of the antibody or antigen-binding fragment thereof, the bifunctional fusion protein, the nucleic acid, the vector, the cell or the pharmaceutical composition of any one of the preceding aspects for the treatment or prophylaxis of diseases.

In another aspect, the present invention relates to the use of the antibody or antigen-binding fragment thereof, the bifunctional fusion protein, the nucleic acid, or the kit of any one of the preceding aspects for detection or diagnosis. Preferably, the use is to diagnose or detect diseases.

In another aspect, the disease is cancer.

In another aspect, the cancer includes gastric cancer, esophageal cancer, head-and-neck cancer, bladder cancer, cervical cancer, sarcoma, cytoma, lung cancer, colon cancer, ovarian cancer, renal cancer, colorectal cancer, pancreatic cancer, liver cancer, melanoma, breast cancer, myeloma, glioma, leukemia, lymphoma and the like.

In another aspect, the present invention relates to a method for preparing the antibody or antigen-binding fragment thereof, or the bifunctional fusion protein of any one of the preceding aspects, which includes transfecting cells with the above vectors, and expressing the antibody or antigen-binding fragment thereof, or the bifunctional fusion protein by the transfected cells; or includes expressing the antibody or antigen-binding fragment thereof, or the bifunctional fusion protein with the above cells.

The antibody or antigen-binding fragment thereof or the bifunctional fusion protein provided in the present invention has one or more of the following advantages: enhanced TGFβ1 binding activity, enhanced PDL1 affinity, enhanced ability of blocking the binding of PDL1 to PD1, enhanced activity of blocking TGFβ1 function, enhanced ability of promoting T cells to secrete IFN-γ, better immunoregulation effect, and better tumor suppression effect.

DESCRIPTION

The present invention will be further described below in connection with specific embodiments. The described embodiments are a part of the embodiments of the present invention, but not all the embodiments. It should be understood that the following examples are given in order to provide a general disclosure and description of how to use the methods and compositions of the present invention to general professionals in the technical field to which the invention belongs, and are not intended to limit the scope of the present invention. Based on the embodiments of the present invention, all other embodiments obtained by those having ordinary skill in the art without the exercise of inventive faculty are within the scope of the present invention.

Materials and Reagents: PDL1 protein (Sinobiological, catalog number: 10084-H08H); PD1 protein (Sinobiological, catalog number: 10377-H08H); TGFβ1 (Sinobiological, catalog number: 10804-HNAC); NaHCO$_3$ (Sinopharm, 10018960); TMB (Beijing Makewonder, catalog number: 1001); STREP/HRP (R&D, catalog number: 890803); HBS-EP+1× buffer (GE, catalog number: BR-1008-26); enzyme label plate (Suzhou Beaver, catalog number: 40301); biosensor chip (GE, catalog number: BR100530); 96-well round bottom plate (Corning, catalog number: 3799); anti Human IgG Fc amino coupling kit (GE, cat #BR-1008-39);

Example 1 Preparation of Bifunctional Fusion Proteins Against PDL1 and TGFβ

1.1 Immunization of PDL1 Protein

Figure 1:
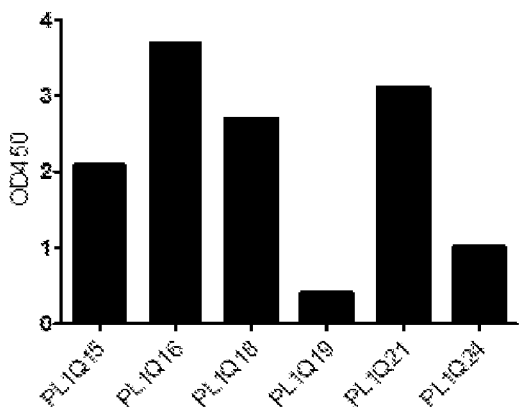
FIG. 1 shows the serum titers of BoAn-hMab1 mice after five immunizations (2500-fold dilution).

The PDL1 protein is emulsified with Freund's complete adjuvant (Sigma, catalog number: F5881-10 ML), Freund's incomplete adjuvant (Sigma, catalog number: F5506-10 ML) or gold adjuvant (Sigma, catalog number: T2684-1 mL) to immunize fully human antibody transgenic mouse BoAn-hMab1 of Boan bio (prepared according to the method described in Chinese Patent CN103571872B). A total of 11 mice including 6 males and 5 females were immunized this time, the age of mice was 6-12 months, a total of 5 immunizations were performed, and 6 mice with higher serum titers were selected for booster immunization with the above PDL1 protein. The serum titers detected by ELISA (2500-fold dilution) are shown in FIG. 1. Herein, the PL1Q15, PL1Q16, PL1Q18, PL1Q19 and PL1Q21 mice were mice immunized with Freund's adjuvant, and the PL1Q24 mouse was a mouse immunized with gold adjuvant.

1.2 Establishment of Phage Library

Six mice with higher serum titers in 1.1 were sacrificed and the spleens were dissected out, the spleens were ground and broken with a syringe rubber stopper and filtered with a filter (FALCON, catalog number: 352350), and the filtered spleen cells were frozen for future use. After RNA extraction, reverse transcription was performed to obtain cDNA, the steps for establishing the phage library refer to the method described in Carlos F. Barbas III, Phage display: A laboratory manual, the variable regions of the heavy and light chains are obtained from the cDNA by PCR, and then single chain Fv (scFv) was obtained by overlapping extension PCR of the variable regions of the heavy chain and the light chain, scFv was digested with Sfi enzyme (NEB, catalog number: #R0123L) and then ligated with plasmid pCOMB3× (BIOVECTOR, Chinese Center, Plasmid Vector Strain Cell Line Gene Collection, 510837) by T4 DNA ligase (Sino Biological), the ligation product was electrotransfected into *E. coli* TG1 competent cells (Lucigen, catalog number: A96595-2), and after incubating the transfected TG1 in 37° C. 220 rpm shaker, the phage was added to infect, the supernatant of the culture was recovered, concentrated and purified to obtain a phage library.

1.3 Screening of Phage Library

Plate screening: preparation of CBS buffer: 1.59 g of $Na_2CO_3$ (Sinopharm, 10019260) and 2.93 g of $NaHCO_3$ were weighed, and the distilled water was added to 1 L to prepare CBS buffer. The PDL1 protein was diluted to 10 μg/mL with CBS buffer, and then added to the screening plate (Costar, 42592) at 100 μg/well, 8 wells were used for each library and the screening plate was left overnight at 4° C.; the protein solution in the well plate was discard the next day, the plate was sealed with 2% BSA (Solarbio, A8010) for 1 h, and phage library ($2\times10^{12}$/well) samples was added to incubate at 37° C. for 2 h, PDL1 specific binding phage was eluted with elution buffer (add 4.2 ml of concentrated hydrochloric acid (Comeo) to 500 ml of ultrapure water and adjust the pH to 2.2 with glycine powder (Biotopped, BG0617-500)) after being washed 4-10 times with PBST (PBS+0.05% Tween20).

Magnetic bead screening: biotinylation of PDL1-mFc protein (Acrobiosystems, catalog number: PD1-H52A3) (molar ratio of protein to biotin is 1:2): the PDL1-mFc protein was changed into 0.1M pH 8.0 $NaHCO_3$, an appropriate amount of biotin (Thermo, 21335) was weighed by precision balance and then dissolved with the ultrapure water, the appropriate amount of dissolved biotin was immediately added to the PDL1-mFc protein solution, and incubated on a rotary mixer in the dark for 40 min, and then the PDL1-mFc protein solution was changed into PBS after labeling. The biotinylated PDL1-mFc protein (3 μg/library) was bound to magnetic beads (Invitrogen Dynabeads M-280 Streptavidin, catalog number: 00355871) (10 μL/library) for 1 h at room temperature, and then incubated with the phage library at room temperature for 2 h after sealing with 2% BSA, and PDL1 specific binding phage was eluted with elution buffer (pH 2.2) after being washed 4-10 times.

Phage clones express scFv through *E. coli*, and then detect the blocking of PDL1/PD1 binding by scFv through ELISA, and clones blocking the activity are retained for constructing subsequent molecules.

ELISA detection of blocking of PDL1/PD1 binding by scFv: the PDL1 protein was diluted to 0.5 μg/mL with pH 9.6 CBS, coated with enzyme-labeled plate, 100 μL/well, and incubated overnight at 4° C.; and 3% defatted milk powder was used for sealing at 37° C. for 1 h after washing the plate. 50 μL of scFv periplasm was added to each well after washing the plate. Then, biotin-labeled PDL1-Fc protein (final concentration was 0.2 μg/mL) was added, 50 μL/well, and incubated at 37° C. for 1 h; STREP/HRP diluted with PBST was added after washing the plate, 100 μL/well, and incubated at 37° C. for 1 h. After washing the plate, 100 μL of TMB was added to each well for color development, after 10 min, 50 μL of 2M $H_2SO_4$ was added to each well to stop the color development, and OD450 was read with a microplate reader.

1.4 Construction and Production of Bifunctional Fusion Protein

Magnetic bead screened clones BA533, BA603, BA613, BA623, BA649, BA669, BA446 and plate screened clone BA705 were sent to Invitrogen Biotechnology Ltd for sequencing. The amino acid sequences of the light chain variable region and the heavy chain variable region of each clone are presented in Table 1 below.

TABLE 1 amino acid sequences of light chain variable region and heavy chain variable region of candidate clones (CDR underlined)

| Clone ID | Light chain variable region sequence | Heavy chain variable region sequence |
|---|---|---|
| BA533 | DIQMTQSPDSLAVSLGERATINCKSS<u>QSVLYSSNNK</u><br><u>NY</u>LAWYQQKPGQPPKLLIY<u>WAS</u>TRESGVPDRFSGSG<br>SGTDFTLTISSLQAEDVAVYYC<u>QQYYSTPLT</u>FGGGT<br>KVEIK (SEQ ID NO: 1)<br>CDR region<br>LCDR1: QSVLYSSNNKNY (SEQ ID NO: 5)<br>LCDR2: WAS (SEQ ID NO: 6)<br>LCDR3: QQYYSTPLT (SEQ ID NO: 7) | EVQLVQSGGGVVQPGRSLRLSCAASG<u>FTFSNYAMHW</u><br>VRQAPGKGLEWVAI<u>ITYAGSNEYYA</u>DSVKGRFTISR<br>DNSKNTLYLQMNSLRPEDTAVYYC<u>ARDRIWVDY</u>WGQ<br>GTLVTVSS (SEQ ID NO: 2)<br>CDR region<br>HCDR1: GFTFSNYA (SEQ ID NO: 8)<br>HCDR2: ITYAGSNE (SEQ ID NO: 9)<br>HCDR3: ARDRIWVDY (SEQ ID NO: 10) |
| BA669 | DIVMTQSPDSLAMSLGERATINCKSS<u>QSVLYNSNNK</u><br><u>NY</u>LAWYQQKPGQPPKLLTY<u>WAS</u>TRESGVPDRFSGSG<br>SGTDFTLTISSLQAEDVAVYYC<u>QQYYSLPLT</u>FGGGT<br>KVEIK (SEQ ID NO: 3)<br>CDR region<br>LCDR1: QSVLYNSNNKNY (SEQ ID NO: 11)<br>LCDR2: WAS (SEQ ID NO: 6)<br>LCDR3: QQYYSLPLT (SEQ ID NO: 12) | QVQLVESGGGVVQPGRSLRLSCAASG<u>FTFSSYAMHW</u><br>VRQAPGKGLEWVALI<u>SYDGSNKYYA</u>DSVKGRFTISR<br>DNSKNTLYLQMNSLRAEDTAVYYC<u>ARDRIYFDY</u>WGQ<br>GTLVTVSS (SEQ ID NO: 4)<br>CDR region<br>HCDR1: GFTFSSYA (SEQ ID NO: 13)<br>HCDR2: ISYDGSNK (SEQ ID NO: 14)<br>HCDR3: ARDRIYFDY (SEQ ID NO: 15) |
| BA603 | DIVMTQSPDSLAVSLGERATINCKSS<u>QSVLYSSNNK</u><br><u>NY</u>LAWYQQKPGQPPKLLIY<u>WAS</u>TRESGVPDRFSGSG<br>SGTDFTLTISSLQAEDVAVYYC<u>QQYYSIPIT</u>FGQGT<br>KLEIK (SEQ ID NO: 25) | EVQLVQSGGGVVQPGRSLRLSCAASG<u>FTFSSYAMHW</u><br>VRQAPGKGLEWVALI<u>SYDGSNKYYA</u>DSVKGRFITSR<br>DNSKNTLYLQMNSLRAEDTAVYYC<u>ARDRIYFDY</u>WGQ<br>GTLVTVSS (SEQ ID NO: 31) |
| BT613 | ELVLTQSPDSLAVSLGERATINCKSS<u>QSVLYSSNNK</u><br><u>NY</u>LAWYQQKPGQPPKLLIY<u>WAS</u>TRESGVPDRFSGSG<br>SGTDFTLTISSLQAEDVAVYYC<u>QQYYSTPLT</u>FGGGT<br>KVDIK (SEQ ID NO: 26) | EVQLVQSGGGVVQPGKSLRLSCAASG<u>FTFSSYSMHW</u><br>VRQAPGKGLEWVALI<u>SFDGSNKYYA</u>DSVKGRFTISR<br>DNSKNTLYLQMTSLRTEDTAVYYC<u>ARDRIYLDY</u>WGQ<br>GTLVTVSS (SEQ ID NO: 32) |
| BA623 | DIQMTQSPDSLAVSLGERATINCKSS<u>QSVLYSSNNK</u><br><u>NY</u>LAWYQQKPGQPPKLLIY<u>WAS</u>IRDSGVPDRFSGSG<br>SGTDFTLTISSLQAEDAAVYYC<u>QQFYSIPLT</u>FGGGT<br>KVEIK (SEQ ID NO: 27) | EVQLVQSGGGVVQPGRSLRLSCAASG<u>FTFSNYAMHW</u><br>VRQAPGKGLEWVALI<u>SYDGSNKYYA</u>DSVKGRFTISR<br>DNSKNTLYLQMNSLRAEDTAVYYC<u>ARDRIYFDY</u>WGQ<br>GTLVTVSS (SEQ ID NO: 33) |

TABLE 1-continued amino acid sequences of light chain variable region and heavy chain
variable region of candidate clones (CDR underlined)

| Clone ID | Light chain variable region sequence | Heavy chain variable region sequence |
|---|---|---|
| BA649 | DIVMTQSPDSLAVSLGERATINCKSSQSVLYSSNNK NYLAWYQQKPGQPPKLLIYWASTRDSGVPDRFSGSG SGTDFTLTISSLQAEDVAVYYCQQYYSIPLTFGGGT KVEIK (SEQ ID NO: 28) | EVQLVQSGGGVVQPGRSLRLSCAASGFTFSSYAMHW VRQAPGKGLEWVALISYDGSNKYYADSVKGRFTISR DNSKNTLYLQMNSLRAEDTAVYYCARDRIYFDYWGQ GTLVTVSS (SEQ ID NO: 31) |
| BA705 | DIVMTQSPDSLAVSLGERATINCKSSQSVLYSSNNK NYLAWYQQKPGQPPKLLIYWASTRESGVPDRFSGSG SGTDFTLTISSLQAEDVAVYYCQQYYSIPLTFGGGT KVEIK (SEQ ID NO: 29) | EVQLVQSGGGVVQPGRSLRLSCAASGITFSNYAMHW VRQAPGKGLEWVALISYDGSNKYYADSVKGRFTISR DNSKNTLYLQMNSLRAEDTAVYYCARDRIYFDYWGQ GTLVTVSS (SEQ ID NO: 34) |
| BA466 | EIVMTQSPDSLAVSLGERATINCKSSQSVLYSSNNK NYLAWYQQKPGQPPKLLIDWASTRESGVPDRFSGSG SGTDFTLTISSLQAEDVAVYYCQQYYSFPLTFGGGT KVEIK (SEQ ID NO: 30) | EVQLVQSGGGVVQPGRSLRLSCAASGFTFSSYAMHW VRQAPGKGLEWVAAISYDGSNKYYADSVKGRFTISR DNSKNTLYLQMNSLRAEDTAVYYCARDRIFFDYWGQ GTLVTVSS (SEQ ID NO: 35) |

Through variable region gene amplification (2*Phanta Max Master Mix, manufacturer: Vazyme, catalog number: P515-AA), signal peptide and variable region overlap extension, homologous recombination (ClonExpress II One Step Cloning Kit, manufacturer: Vazyme, catalog number: C112-01) and other methods, the nucleotide sequence fragment encoding VH was finally inserted into the vector pCDNA3.4 (Life Technology) with the nucleotide sequence encoding SEQ ID NO: 18 wherein SEQ ID NO: 18 contains the sequences of the heavy chain constant region of the IgG1 antibody and the TGFβRII sequence which are linked by $(G_4S)_4G$ (SEQ ID NO: 24), the nucleotide sequence fragment encoding VL was inserted into the vector pCDNA3.4 (Life Technology) with the nucleotide sequence encoding the light chain constant region amino acid sequence (SEQ ID NO: 16) of the antibody, then HEK293 cells were transfected, and incubated in 37° C.\8% $CO_2$\125 rpm shaker for 6 to 7 days, and finally the culture supernatant was purified by Protein A filler to obtain the clone of bifunctional fusion protein in Table 2 for subsequent detection.

TABLE 2

Clones of bifunctional fusion protein against PDL1-TGFβ

| | | |
|---|---|---|
| PLTGBQ19-BA533-IgG1 | PLTGBQ24-BA603-IgG1 | PLTGBQ16-BA466-IgG1 |
| PLTGBQ21-BA649-IgG1 | PLTGBH03-BT613-IgG1 | PLTGBQ24-BA705-IgG1 |
| PLTGBQ21-BA669-IgG1 | PLTGBQ21-BA623-IgG1 | / |

Production of control bifunctional fusion protein: M7824 bifunctional fusion protein of the company Merck is anti-PDL1 antibody Avelumab linked to TGFβRII by $(G_4S)_4G$ (SEQ ID NO: 24), some phase I and phase II clinical trials have been completed, and it has performed well in a variety of solid tumors. The amino acid sequence of the variable region of Avelumab of the company Merck (the sequence of the heavy chain variable region is SEQ ID NO: 19, the sequence of the light chain variable region is SEQ ID NO: 20) is determined by IMGT database, the complete gene is synthesized and then inserted into the vector pCDNA3.4 for expression in HEK293 cells, and the purified bifunctional fusion protein is named PLTGB-M7824-IgG1 (the sequence of the heavy chain variable region is SEQ ID NO: 19, the sequence of the light chain variable region is SEQ ID NO: 20, the sequence of the light chain constant region is SEQ ID NO: 21, and the sequence of the heavy chain constant region and TGFβRII is SEQ ID NO: 18).

1.5 ELISA Detection of Blocking of PDL1-PD1 Binding by Bifunctional Fusion Protein The PD1 protein was diluted to 0.5 μg/mL with CBS at pH 9.6, and then was coated with enzyme-labeled plate, 100 μL/well, and incubated overnight at 4° C.; 3% defatted milk powder was used for sealing at 37° C. for 1 h after washing the plate; PBST (PBS+0.05% Tween20) was added to dilute the bifunctional fusion protein to different concentrations (0.5 μg/mL, 0.25 μg/mL, 0.125 μg/mL, 0.0625 μg/mL, 0.03125 μg/mL, 0.015625 μg/mL) after washing the plate, 50 μL/well, biotin-labeled PDL1-Fc protein (final concentration is 0.2 μg/mL) was then added, 50 μL/well, and incubated at 37° C. for 1 h; STREP/HRP diluted with PBST was added, 100 μL/well, and incubated at 37° C. for 1 h. TMB was added for color development after washing the plate, and 50 μL of 2M $H_2SO_4$ was added to each well to stop the color development after 10 min, OD450 was read on a microplate reader. The results show that the candidate bifunctional fusion proteins of the present invention (PLTGBQ16-BA466-IgG1, PLTGBQ19-BA533-IgG1, PLTGBQ24-BA603-IgG1, PLTGBQ21-BA623-IgG1, PLTGBQ21-BA649-IgG1, PLTGBQ21-BA669-IgG1, PLTGBQ24-BA705-IgG1, PLTGBH03-BT613-IgG1) can effectively block the binding of PD1 to PDL1.

1.6 ELISA Detection of Binding of Bifunctional Fusion Protein to TGFβ1 Protein

The TGFβ1 was diluted to different concentrations (0.2 μg/mL, 0.05 μg/mL, 0.0125 μg/mL) with pH 9.6 CBS, and then was coated with enzyme-labeled plate respectively, 100 μL/well, and incubated overnight at 4° C.; 3% defatted milk powder was used for sealing at 37° C. for 1 h after washing the plate; 100 μL of PBST (PBS+0.05% Tween20) diluted candidate bifunctional fusion protein (1 μg/mL) was added to each well after washing the plate, and incubated at 37° C. for 1 h; then goat anti-human IgG/HRP was added and incubated at 37° C. for 1 h; TMB is added for color development after washing the plate, and 50 μL of 2M $H_2SO_4$ was added to each well to stop the color development after 10 min, OD450 was read on the microplate reader. The results are shown in Table 3 and FIG. 2.

The candidate bifunctional fusion proteins PLTGBQ19-BA533-IgG1 and PLTGBQ21-BA669-IgG1 have higher OD values at various concentrations than the control group PLTGB-M7824-IgG1, indicating that the candidate bifunctional fusion proteins have better binding ability for TGFβ1.

Furthermore, it is predicted that the candidate bifunctional fusion proteins PLTGBQ19-BA533-IgG1 and PLTGBQ21-BA669-IgG1 can block the TGF pathway better than the control group PLTGB-M7824-IgG1, and have better immune regulation and anti-tumor properties in clinical.

TABLE 3

Figure 2:
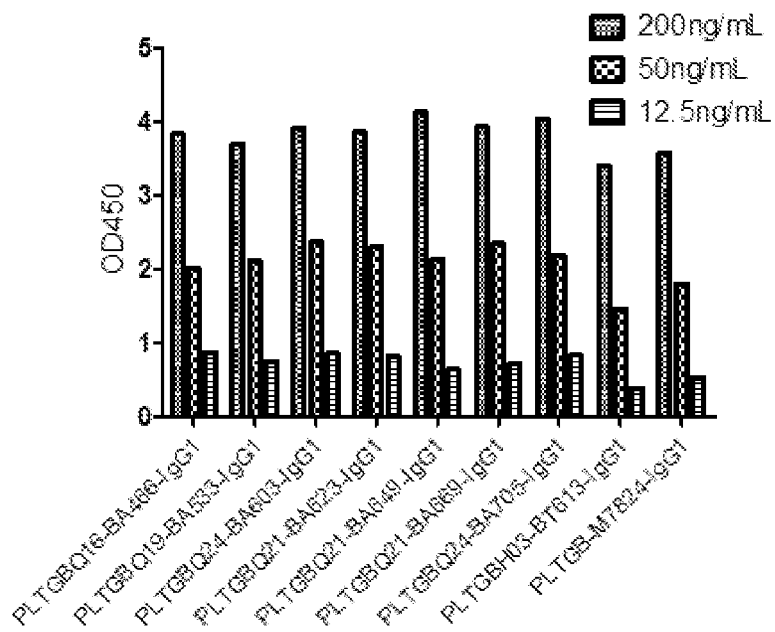
FIG. 2 shows the binding of the bifunctional fusion protein to the TGFβ1 protein.

Data of ELISA detection of binding of bifunctional fusion protein to TGFβ1 protein (corresponding to FIG. 2)

| | OD450 at different TGFβ1 concentrations | | |
|---|---|---|---|
| Name | TGFβ1 concentration 0.2 µg/mL | TGFβ1 concentration 0.05 µg/mL | TGFβ1 concentration 0.0125 µg/mL |
| PLTGBQ16-BA466-IgG1 | 3.829 | 2.009 | 0.88 |
| PLTGBQ19-BA533-IgG1 | 3.699 | 2.113 | 0.758 |
| PLTGBQ24-BA603-IgG1 | 3.921 | 2.367 | 0.861 |
| PLTGBQ21-BA623-IgG1 | 3.854 | 2.302 | 0.813 |
| PLTGBQ21-BA649-IgG1 | 4.122 | 2.136 | 0.636 |
| PLTGBQ21-BA669-IgG1 | 3.93 | 2.351 | 0.728 |
| PLTGBQ24-BA705-IgG1 | 4.038 | 2.184 | 0.836 |
| PLTGBH03-BT613-IgG1 | 3.403 | 1.46 | 0.388 |
| PLTGB-M7824-IgG1 | 3.572 | 1.807 | 0.537 |

Example 2 Characterization of Bifunctional Fusion Protein 2.1 Production of Bifunctional Fusion Protein ExpiCHO (Thermo, catalog number: A29129) express system is used to transfect and express the bifunctional fusion protein, and protein A (GE, Mabselect SuRe) column is used to purify the supernatant: the cell culture fluid was centrifuged at 4500 g and filtered with a 0.45 µm filter, the target bifunctional fusion protein was eluted with 0.1M pH3.2 glycine buffer after loading and equilibrating, and neutralized with pH8.0 1M Tris. Size exclusion chromatography (Shanghai Bestchrom, catalog number: AG319109) is used to purify: equilibrate the column with 1.5 CV of buffer, load the sample, the sample volume is not more than 3% CV, continue to rinse with buffer and collect the target bifunctional fusion protein after peak appears.

2.2 Mixed Lymphocyte Reaction/MLR Detection of Bifunctional Fusion Protein Activity RPMI 1640 (Gibco, catalog number: 11875-093), FBS (Gibco, catalog number: 10091-148), HEPES (Solarbio, catalog number: H1090) were mixed according to 90:10:1 to prepare a complete medium, DC cells (ALLCELLS, catalog number: PB-DC001F-0.3M) and CD4+T cells (ALLCELLS, catalog number: PB009-2F-C-3M) were resuspended with the complete medium respectively, and then added to 96-well round bottom plate according to a cell ratio of 1:10, and the final volume is 150 µL/well. The bifunctional fusion protein was diluted, with the complete medium, two concentrations: 4 µg/mL and 0.4 µg/mL, and added into the cell wells respectively, 50 µL/well, and the final volume is 200 µL. After being cultured for 5 days, the culture supernatant was detected with IFN-γ kit (cisbio, catalog number: 62HIFNGPEG). The detection results are shown in Table 4 and FIG. 3.

The candidate bifunctional fusion proteins PLTGBQ19-BA533-IgG1 and PLTGBQ21-BA669-IgG1 have higher IFN-γ secretion values at the same concentration than the control group PLTGB-M7824-IgG1.

Furthermore, it is predicted that the candidate bifunctional fusion proteins PLTGBQ19-BA533-IgG1 and PLTGBQ21-BA669-IgG1 may have better immune regulation and anti-tumor properties than the control group PLTGB-M7824-IgG1.

TABLE 4

Figure 3:
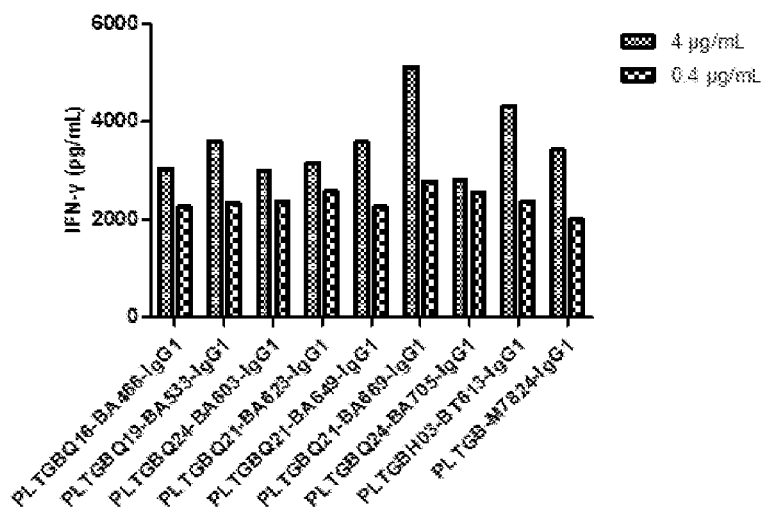
FIG. 3 shows that the bifunctional fusion protein promotes secretion of IFN-γ by CD4+T.

Data of Mixed Lymphocyte Reaction/MLR detection of bifunctional fusion protein activity (corresponding to FIG. 3)

| | IFN-γ secretion value at different bifunctional fusion protein concentrations | |
|---|---|---|
| Name | bifunctional fusion protein concentration (4 µg/mL) | bifunctional fusion protein concentration (0.4 µg/mL) |
| PLTGBQ16-BA466-IgG1 | 3029.907 | 2262.317 |
| PLTGBQ19-BA533-IgG1 | 3594.345 | 2336.045 |
| PLTGBQ24-BA603-IgG1 | 2983.494 | 2355.715 |
| PLTGBQ21-BA623-IgG1 | 3147.502 | 2572.435 |
| PLTGBQ21-BA649-IgG1 | 3589.663 | 2269.363 |
| PLTGBQ21-BA669-IgG1 | 5117.964 | 2781.657 |
| PLTGBQ24-BA705-IgG1 | 2801.897 | 2550.59 |
| PLTGBH03-BT613-IgG1 | 4328.078 | 2365.794 |
| PLTGB-M7824-IgG1 | 3423.783 | 1996.965 |

2.3 SPR Detection of Affinity of Bifunctional Fusion Protein and PDL1 Protein

Antibody binding kinetics adopts BIAcore8K instrument to detect. Anti-human IgG antibody was coupled to a CM5 biosensor chip by the anti-human IgG Fc amino coupling kit to obtain approximately 1000 RU (response units). The PDL1 was diluted to 50 nM with HBS-EP+1× buffer, and then diluted 2-fold to a total of 5 concentrations (50 nM, 25 nM, 12.5 nM, 6.25 nM, 3.125 nM), and a blank control was set. The measurement steps and conditions were as follows: bifunctional fusion protein sample injection 2 µg/mL, sample injection time 70 s, flow rate 5 µl/min, stability time 5 s; PDL1 protein binding and dissociation: binding 60 s, flow rate 30 µl/min, dissociation 450 s; regeneration: regeneration was performed for 30 s with 3M $MgCl_2$ buffer, starting for 3 times. The association constant (ka) and dissociation constant (kd) were calculated using a one-to-one Languir model (BIAcore Evaluation Software version 3.2), and the equilibrium dissociation constant KD is calculated from kd/ka. The affinity data of each bifunctional fusion protein is shown in Table 5.

The results show that the candidate bifunctional fusion proteins PLTGBQ19-BA533-IgG1 and PLTGBQ21-BA669-IgG1 of the present invention have a PDL1 affinity that is substantially equivalent to that of the control group PLTGB-M7824-IgG1. Wherein, PLTGBQ19-BA533-IgG1 has better PDL1 affinity than the control group.

TABLE 5

Affinity of bifunctional fusion protein and PDL1 protein

| Name | ka (1/Ms) | kd (1/s) | KD (M) |
|---|---|---|---|
| PLTGBQ16-BA466-IgG1 | 1.14E+06 | 2.32E−03 | 2.03E−09 |
| PLTGBQ19-BA533-IgG1 | 1.50E+06 | 7.95E−04 | 5.29E−10 |
| PLTGBQ24-BA603-IgG1 | 1.70E+06 | 1.64E−03 | 9.63E−10 |
| PLTGBQ21-BA623-IgG1 | 1.34E+06 | 1.79E−03 | 1.34E−09 |
| PLTGBQ21-BA649-IgG1 | 1.85E+06 | 1.67E−03 | 9.04E−10 |
| PLTGBQ21-BA669-IgG1 | 1.78E+06 | 1.36E−03 | 7.64E−10 |
| PLTGBQ24-BA705-IgG1 | 1.45E+06 | 8.37E−04 | 5.77E−10 |
| PLTGBH03-BT613-IgG1 | 1.39E+06 | 1.01E−03 | 7.30E−10 |
| PLTGB-M7824-IgG1 | 4.98E+05 | 3.00E−04 | 6.03E−10 |

Figure 4:
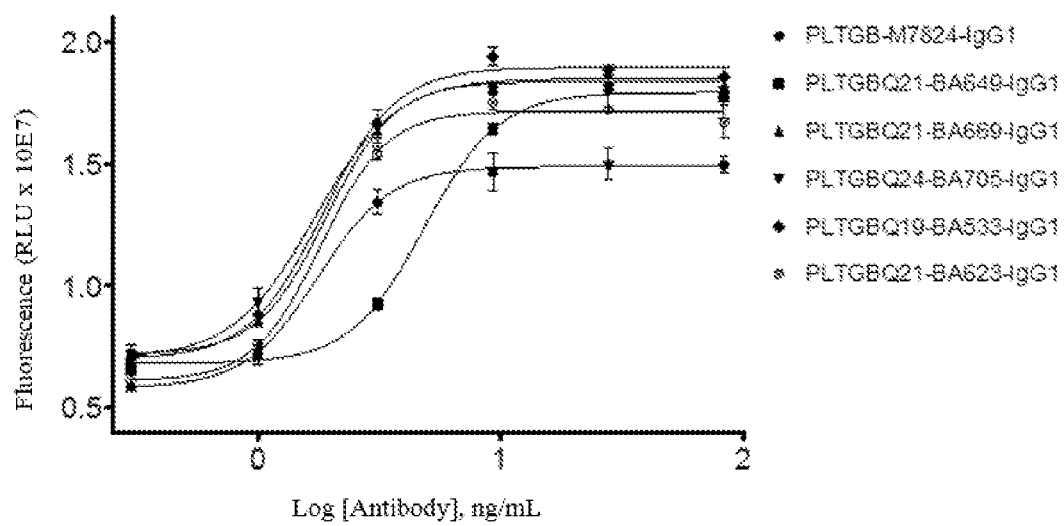
FIG. 4 shows the blocking effect of the bifunctional fusion protein on the TGFβ1 function.

2.4 Detection of Blocking Effect of Bifunctional Fusion Protein on TGFβ1 Function by MV-1-Lu Cells EMEM (ATCC, catalog number: 30-2003), FBS (Gibco, catalog number: 10099-141) and HEPES (Solarbio, catalog number: H1090) were mixed according to 90:10:1 to prepare a complete medium, MV-1-Lu cells were resuspended with the complete medium, and added to white 96-well plate (Corning, catalog number: 3917), 50 μL/well, 2000 cells/well. The bifunctional fusion protein was diluted to 333.3 ng/mL with the complete medium, and then diluted three times in sequence, a total of 6 concentrations, added into the cell wells, 25 μL/well. TGF β1 was diluted to 2 ng/ml with complete medium and added into the cell wells, 25 μL/well. The final concentrations of the bifunctional fusion protein: 83.3 ng/mL, 27.8 ng/mL, 9.26 ng/mL, 3.09 ng/mL, 1.03 ng/mL and 0.34 ng/mL. After being cultured for 4 days, the fluorescence value (the fluorescence value can represent the number of cells) of the 96-well plate was detected with CellTiter-Glo kit (Promega, catalog number: G7571), and the detection results are shown in FIG. 4.

It can be seen that the candidate bifunctional fusion proteins PLTGBQ19-BA533-IgG1 and PLTGBQ21-BA669-IgG1 have better activity in blocking TGFβ1 function than the control group PLTGB-M7824-IgG1.

Furthermore, it is predicted that the candidate bifunctional fusion proteins PLTGBQ19-BA533-IgG1 and PLTGBQ21-BA669-IgG1 can block the TGF pathway better than the control group PLTGB-M7824-IgG1, and have better immune regulation and anti-tumor properties.

Example 3 Efficacy Test of Anti-PD-L1 Monoclonal Antibody in Mouse MC38-hPDL1 Colon Cancer Model The IgG1 monoclonal antibody corresponding to the bifunctional fusion protein was constructed, the monoclonal antibody corresponding to PLTGBQ19-BA533-IgG1 is BA533-IgG1 (the sequence of the heavy chain variable region is SEQ ID NO: 2, the sequence of the light chain variable region is SEQ ID NO: 1, the sequence of the light chain constant region is SEQ ID NO: 16, and the sequence of the heavy chain constant region is SEQ ID NO: 17); the monoclonal antibody corresponding to PLTGBQ21-BA669-IgG1 is BA669-IgG1 (the sequence of the heavy chain variable region is SEQ ID NO: 4, the sequence of the light chain variable region is SEQ ID NO: 3, the sequence of the light chain constant region is SEQ ID NO: 16, and the sequence of the heavy chain constant region is SEQ ID NO: 17); and the monoclonal antibody corresponding to PLTGB-M7824-IgG is Avelumab (the sequence of the heavy chain variable region is SEQ ID NO: 19, the sequence of the light chain variable region is SEQ ID NO: 20, the sequence of the light chain constant region is SEQ ID NO: 21, and the sequence of the heavy chain constant region is SEQ ID NO: 17).

Mouse colon cancer MC38-hPD-L1 cells was purchased from Beijing Biocytogen Co., Ltd. The culture conditions are that 10% FBS (Gibco, catalog number: 10099-141C) and 1% P/S (Gibco, catalog number: 15070-063) are added in DMEM (Gibco, catalog number: 11965-092) medium, and cultured in an incubator with 5% $CO_2$ at 37° C. The subculture is performed 2-3 times per week. B-hPD-L1 humanized mouse, female, 6-8 weeks old, purchased from Jiangsu Biocytogen Co., Ltd.

The MC38-hPD-L1 cells in good condition were collected, resuspended and mixed in PBS, the cell concentration was adjusted to $5 \times 10^6$/ml, and 0.1 ml of cell suspension was inoculated subcutaneously on the dorsal limb of each mouse. When the average tumor volume reached 87 mm3, randomization was started. There were 7 groups of 6 mice each, administration was started on the day of grouping, and anti-PD-L1 monoclonal antibody was diluted with PBS, each antibody had two doses: 3 mg/kg and 10 mg/kg, administered by intraperitoneal injection once every 2 days, the same volume of PBS was given in solvent control group as a control. The mice were weighted and the tumor volume was measured 2-3 times per week, tumor volume ($mm^3$) =0.5×long diameter×short diameter$^2$. When the tumor volume of the control group reached 2000 $mm^3$, the mice were euthanized, and the tumors were stripped and weighed. The results are shown in FIG. 5A, FIG. 5B, FIG. 5C and Tables 6 and 7.

Figure 5A:
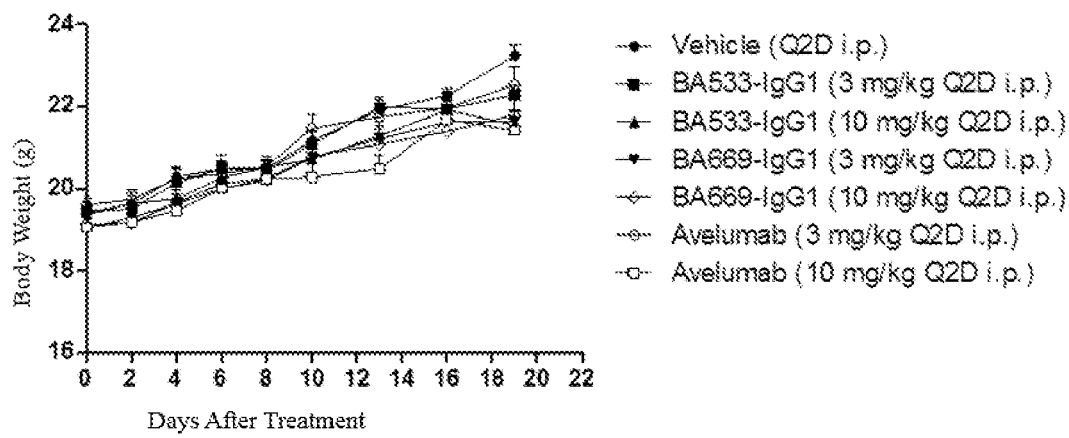
FIG. 5A shows body weights of the MC38-hPD-L1 tumor model mice.

As shown in FIG. 5A, the body weight of the mice increases steadily without any adverse reactions.

Figure 5B:
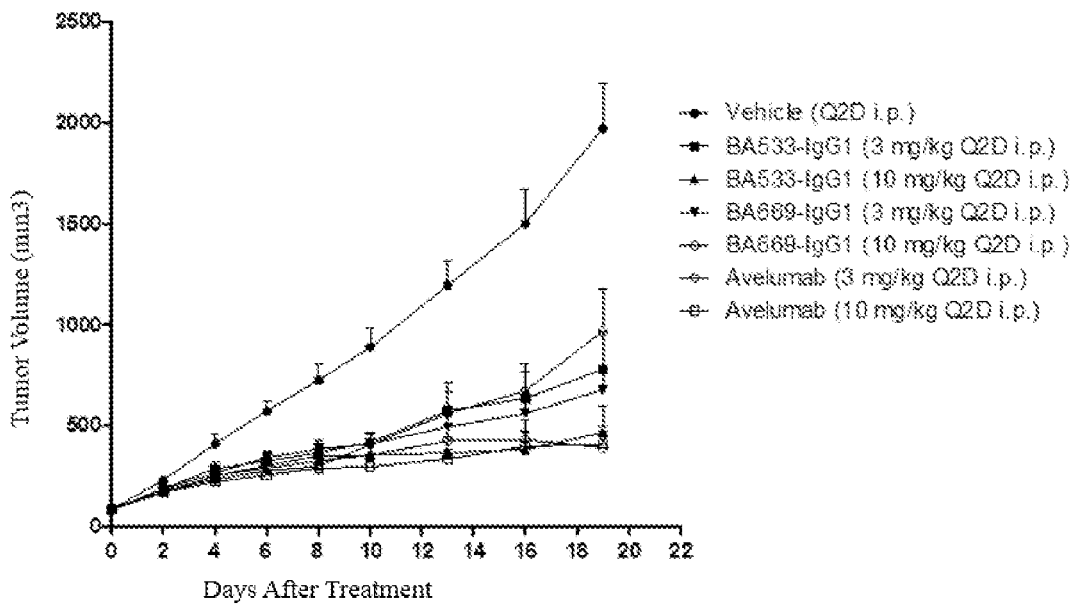
FIG. 5B shows tumor volumes of the MC38-hPD-L1 tumor model mice.
Figure 5C:
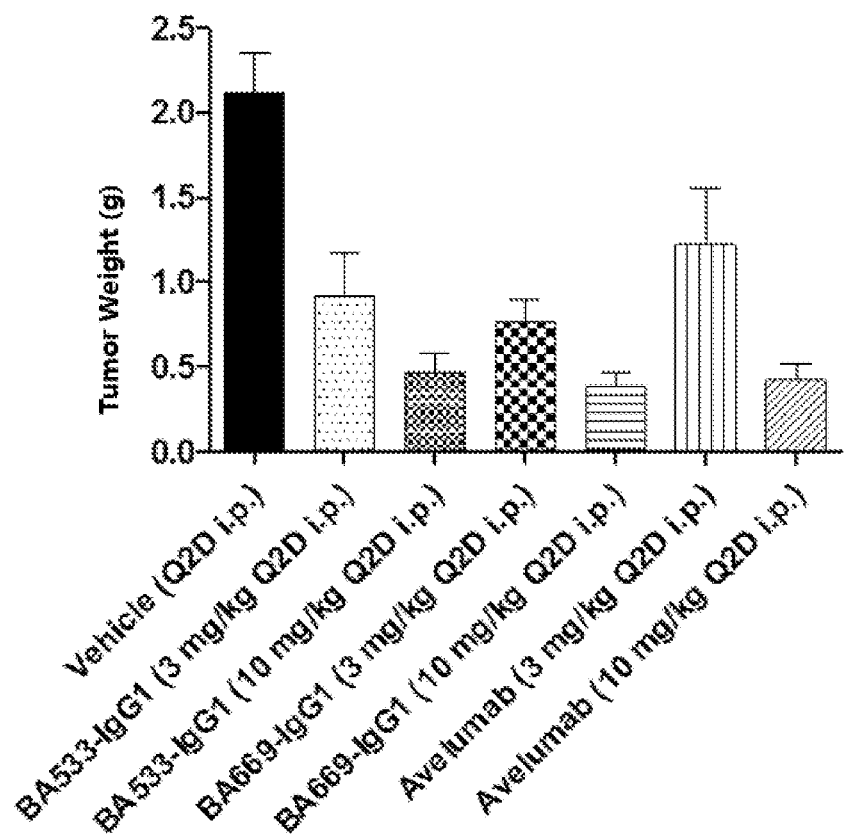
FIG. 5C shows tumor weights of the MC38-hPD-L1 tumor model mice

As shown in FIG. 5B and FIG. 7C, when BA533-IgG1, BA669-IgG1, and Avelumab were administered at a dose of 10 mg/kg, they could significantly inhibit the growth of the tumors of the mice MC38-hPD-L1, and the relative tumor suppression rate TGI (%)≥80%, there is no statistical difference between the three. When BA533-IgG1, BA669-IgG1, and Avelumab were administered at a dose of 3 mg/kg, the tumor suppression rates of BA533-IgG1 and BA669-IgG1 were superior to Avelumab.

The above results indicate that, at low doses, the candidate antibodies have better tumor suppression effect than the control antibody, and at high doses, they also have comparable tumor suppression effects.

TABLE 6

Tumor volume data of MC38-hPD-L1 tumor model mice (average value ± SEM) (corresponding to FIG. 5B)

| Group | Tumor volume at endpoint ($mm^3$) |
| --- | --- |
| Vehicle(Q2D, i.p.) | 1972 ± 224 |
| BA533-IgG1(3 mg/kg, Q2D, i.p.) | 780 ± 185 |
| BA669-IgG1(3 mg/kg, Q2D, i.p.) | 679 ± 113 |
| Avelumab(3 mg/kg, Q2D, i.p.) | 969 ± 208 |
| BA533-IgG1(10 mg/kg, Q2D, i.p.) | 465 ± 131 |
| BA669-IgG1(10 mg/kg, Q2D, i.p.) | 392 ± 83 |
| Avelumab(10 mg/kg, Q2D, i.p.) | 408 ± 90 |

TABLE 7

Tumor weight data of MC38-hPD-L1 tumor model (average value ± SEM) (corresponding to FIG. 5C)

| Group | Tumor weight at endpoint (g) |
| --- | --- |
| Vehicle (Q2D, i.p.) | 2.12 ± 0.24 |
| BA533-IgG1 (3 mg/kg, Q2D, i.p.) | 0.92 ± 0.26 |
| BA669-IgG1 (3 mg/kg, Q2D, i.p.) | 0.77 ± 0.13 |
| Avelumab (3 mg/kg, Q2D, i.p.) | 1.22 ± 0.33 |
| BA533-IgG1 (10 mg/kg, Q2D, i.p.) | 0.46 ± 0.12 |
| BA669-IgG1 (10 mg/kg, Q2D, i.p.) | 0.39 ± 0.08 |
| Avelumab (10 mg/kg, Q2D, i.p.) | 0.42 ± 0.09 |

The invention claimed is:

1. An antibody or antigen-binding fragment thereof, comprising (1) three heavy chain complementarity determining regions (HCDR1, HCDR2 and HCDR3), wherein HCDR1 comprises SEQ ID NO: 8, HCDR2 comprises SEQ ID NO: 9, and HCDR3 comprises SEQ ID NO: 10 and (2) three light chain complementarity determining regions (LCDR1, LCDR2 and LCDR3), wherein LCDR1 comprises SEQ ID NO: 5, LCDR2 comprises SEQ ID NO: 6, and LCDR3 comprises SEQ ID NO: 7, wherein the antibody or antigen-binding fragment thereof binds to PDL1.

2. A antibody or antigen-binding fragment thereof, comprising a heavy chain variable region with an amino acid sequence of SEQ ID NO: 2 and a light chain variable region with an amino acid sequence of SEQ ID NO: 1, wherein the antibody or antigen-binding fragment thereof binds to PDL1.

3. The antibody or antigen-binding fragment thereof of claim 1, wherein the antibody or antigen-binding fragment thereof a comprises a monoclonal antibody, a chimeric antibody, a humanized antibody, a Fab fragment, a Fab' fragment, a F(ab')2 fragment, a Fv fragment, a scFv fragment, or a dsFv fragment.

4. A bifunctional fusion protein comprising the antibody or antigen-binding fragment thereof of claim 1 and a TGFβRII fragment, wherein the antibody or antigen-binding fragment thereof and the TGFβRII fragment are linked by a linker.

5. A pharmaceutical composition, comprising the antibody or antigen-binding fragment thereof of claim 1.

6. An antibody or antigen-binding fragment thereof, comprising:
a light chain variable region comprising LCDR1, LCDR2, and LCDR3 that are identical to LCDR1, LCDR2, and LCDR3 of SEQ ID NO: 1; and
a heavy chain variable region comprising HCDR1, HCDR2, and HCDR3 that are identical to HCDR1, HCDR2, and HCDR3 of SEQ ID NO: 2 wherein the antibody or antigen binding fragment thereof binds to PDL1.

* * * * *

UNITED STATES PATENT AND TRADEMARK OFFICE
CERTIFICATE OF CORRECTION

| | | |
|---|---|---|
| PATENT NO. | : 12,325,748 B2 | Page 1 of 1 |
| APPLICATION NO. | : 17/601891 | |
| DATED | : June 10, 2025 | |
| INVENTOR(S) | : Deyong Song, Hongguang Xu and Zhen Han | |

It is certified that error appears in the above-identified patent and that said Letters Patent is hereby corrected as shown below:

On the Title Page

Column 2 (Abstract), Line 9, Delete "TGFβ 1," and insert -- TGFβ1, --.

In the Claims

In Column 41, Line 49, In Claim 1, after 10 insert -- ; --.

In Column 41, Line 55 (Approx.), In Claim 2, delete "A" and insert -- An --.

In Column 41, Line 57 (Approx.), In Claim 2, after 2 insert -- . --.

In Column 41, Line 63 (Approx.), In Claim 3, after thereof delete "a".

In Column 42, Line 60 (Approx.), In Claim 6, after 2 insert -- , --.

Signed and Sealed this
Twenty-third Day of December, 2025

John A. Squires
*Director of the United States Patent and Trademark Office*